US010261086B2

(12) United States Patent
Menon et al.

(10) Patent No.: US 10,261,086 B2
(45) Date of Patent: Apr. 16, 2019

(54) DIFFERENTIAL CEREBROSPINAL FLUID REACTIVITY TO PFDN5-ALPHA FOR DETECTION OF B-CELL ACUTE LYMPHOBLASTIC LEUKEMIA

(71) Applicant: AMRITA VISHWA VIDYAPEETHAM, Ponekkara Po, Kochi (IN)

(72) Inventors: Krishna Kumar N. Menon, Kochi (IN); Tessy Xavier, Kochi (IN); Adhwyth Haridasan, Kochi (IN)

(73) Assignee: AMRITA VISHWA VIDYAPEETHAM, Kochi (IN)

( * ) Notice: Subject to any disclaimer, the term of this patent is extended or adjusted under 35 U.S.C. 154(b) by 490 days.

(21) Appl. No.: 15/314,491

(22) PCT Filed: Jan. 10, 2014

(86) PCT No.: PCT/IB2014/058167
§ 371 (c)(1),
(2) Date: Nov. 28, 2016

(87) PCT Pub. No.: WO2014/108855
PCT Pub. Date: Jul. 17, 2014

(65) Prior Publication Data
US 2017/0138948 A1 May 18, 2017

(30) Foreign Application Priority Data

Jan. 10, 2013 (IN) .............................. 155/CHE/2013

(51) Int. Cl.
*G01N 33/574* (2006.01)
(52) U.S. Cl.
CPC . *G01N 33/57426* (2013.01); *G01N 33/57488* (2013.01); *G01N 2333/4703* (2013.01)
(58) Field of Classification Search
None
See application file for complete search history.

(56) References Cited

U.S. PATENT DOCUMENTS

| | | | |
|---|---|---|---|
| 2006/0084071 A1 | 4/2006 | Muchowski et al. | |
| 2013/0244897 A1* | 9/2013 | Lueking ............... | C12Q 1/6883 506/9 |

FOREIGN PATENT DOCUMENTS

| | | | |
|---|---|---|---|
| EP | 2437060 | * | 4/2012 |
| WO | 9213076 A1 | | 8/1992 |
| WO | 03038439 A2 | | 5/2003 |
| WO | 03039443 A2 | | 5/2003 |
| WO | 03083140 A2 | | 10/2003 |
| WO | 2008138578 A2 | | 11/2008 |

OTHER PUBLICATIONS

Haigo et al (Journal of Cellular Biochemistry, 20016, 97:145-155).*
Babel et al (Molecular & Cellular Proteomics, 2009, 8:2382-2395).*
Fujioka Y., et al., "MM-1, a c-Myc-binding Protein, is a Candidate for a Tumor Suppressor in Leukemia/lymphoma and Tongue Cancer", The Journal of Biological Chemistry, 2001, vol. 276 (48), pp. 45137-45144.
Hansen P.B., et al., "Cerebrospinal Fluid Beta-2-microglobulin in Adult Patients with Acute Leukemia or Lymphoma: a Useful Marker in Early Diagnosis and Monitoring of cns-involvement", Acta Neurologica Scandinavica, 1992, vol. 85(3), pp. 224-227.
International Preliminary Report on Patentability for Application No. PCT/IB2014/058167, dated Jul. 14, 2015, 15 pages.
International Search Report and Written Opinion for Application No. PCT/IB2014/058167, dated Apr. 29, 2014, 22 pages.
Lee Y., et al., "Prefoldin 5 is Required for Normal Sensory and Neuronal Development in a Murine Model", The Journal of Biological Chemistry, 2011, vol. 286 (1), pp. 726-736.
Mori K., et al., "MM-1, a Novel c-Myc-associating Protein that Represses Transcriptional Activity of c-Myc", The Journal of Biological Chemistry, 1998, vol. 273 (45), pp. 29794-29800.
Satou A., et al., "A Novel Transrepression Pathway of c-Myc. Recruitment of a Transcriptional Corepressor Complex to c-Myc by MM-1, a c-Myc-binding Protein", The Journal of Biological Chemistry, 2001, vol. 276 (49), pp. 46562-46567.

* cited by examiner

*Primary Examiner* — Laura B Goddard
(74) *Attorney, Agent, or Firm* — Convergence Intellectual Property Law P.C.; Jonathan Garfinkel

(57) ABSTRACT

A method of managing treatment in a patient with B-cell acute lymphoblastic leukemia (B-ALL) for central nervous system (CNS) leukemia is disclosed. The method comprises obtaining cerebrospinal fluid (CSF) from the patient, obtaining a cell proteome including PFDN5-α from the patient, detecting reactivity of CSF against the PFDN5-α, comparing reactivity profile of CSF against the PFDN5-α at diagnosis and during treatment, and determining the status of proliferation of leukemia in the patient depending on the comparison. The method further comprises treating the patient for CNS leukemia based on the status of proliferation.

4 Claims, 7 Drawing Sheets
Specification includes a Sequence Listing.

DIFFERENTIAL CEREBROSPINAL FLUID REACTIVITY TO PFDN5-ALPHA FOR DETECTION OF B-CELL ACUTE LYMPHOBLASTIC LEUKEMIA

CROSS-REFERENCES TO RELATED APPLICATIONS

This application is a 35 U.S.C. § 371 national stage filing of PCT Patent Application Number PCT/IB2014/058167, filed Jan. 10, 2014, which claims the benefit and priority of the following: Indian patent application no. 155/CHE/2013, filed on Jan. 10, 2013, the full disclosure of which is incorporated herein by reference.

FIELD OF THE INVENTION

This disclosure relates generally to medical diagnostics and particularly to a method of identifying the prevalence and relapse of B-cell-acute lymphoblastic leukemia.

DESCRIPTION OF THE RELATED ART

Acute lymphoblastic leukemia is one of the curable forms of leukemia. However, relapse occurs in 20% of the patients at extramedullar sites such as central nervous system (CNS) leading to CNS leukemia. Without effective CNS-directed therapy, 50% to 70% of children originally diagnosed with lymphoblastic leukemia will develop leukemia within the CNS. Currently, intrathecal injection of drugs is given prophylactically to patients diagnosed with B-ALL to prevent the CNS involvement. Prophylactic treatment can be avoided if prediction of CNS involvement is possible. The prophylactic treatment results in grievous side effects such as secondary neoplasms, neurocognitive dysfunction, neurotoxic effects, many endocrine diseases, growth impairment and thyroid dysfunction.

The discovery of biomarkers that predicts the progress of disease, classification into diverse risk groups, and identification of CNS malignancy in populations plays an important role in the adept analysis and designing of better treatment options. PFDN5-α, a member of the prefoldin alpha subunit family, is a heterohexameric co-chaperone which primarily aids in proper folding of nascent proteins, primarily actin and tubulin. PFDN5-α otherwise known as myc-modulating (MM-1) protein, has been reported to have a trans-repression activity towards the proto-oncogene c-myc. Human PFDN5-α is a 154 amino acid protein, with the genomic position at 12q12. Repression of E-box mediated transcription of the proto-oncogene c-myc, on interaction with PFDN5-α, implies its critical role in cancers (K Mori, 1998; Satou, 2001). Mutations of this gene have been reported to be present in 50-60% of leukemia/lymphomas and in more than 75% of squamous cell carcinoma of tongue cancer (Y Fujioka, 2001). Mutant murine PFDN5-α was demonstrated to have a role in CNS abnormalities (YS Lee, 2011).

The invention described herein provides for methods by which early detection of the possibility of developing CNS leukemia in B-ALL patients.

SUMMARY OF THE INVENTION

A method of detecting leukemia of the central nervous system (CNS) in B-cell acute lymphoblastic leukemia patients is disclosed, comprising, obtaining a sample of cerebrospinal fluid (CSF) from a patient, applying the sample to a leukemic cell proteome including PFDN5-α from the patient, detecting reactivity of CSF with the PFDN5-α and determining the status of proliferation of leukemia in the patient depending on the level of reactivity. The patient is detected as negative for central nervous system leukemia if the reactivity of CSF with the PFDN5-α is positive and the patient is detected as positive for CNS leukemia if the reactivity of CSF with the PFDN5-α is below a threshold of significance. Detecting reactivity of CSF with the PFDN5-α may comprise testing using far western blot test, a pull down assay, an ELISA test or immunoprecipitation.

A method of managing treatment in a patient with B-cell acute lymphoblastic leukemia (B-ALL) for central nervous system (CNS) leukemia is disclosed, comprising obtaining cerebrospinal fluid (CSF) from the patient, obtaining a cell proteome including PFDN5-α from the patient, detecting reactivity of CSF against the PFDN5-α, comparing reactivity profile of CSF against the PFDN5-α at diagnosis and during treatment, determining the status of proliferation of leukemia in the patient depending on the comparison, and treating the patient for CNS leukemia based on the status of proliferation. The patient is detected as negative for central nervous system leukemia if the reactivity of CSF with the PFDN5-α is positive and the patient is detected as positive for CNS leukemia if the reactivity of CSF with the PFDN5-α is below a threshold of significance. The method of may comprise detecting reactivity of CSF with the PFDN5-α using far western blot test, a pull down assay, an ELISA test or immunoprecipitation.

A method of obtaining a high level of expression of PFDN5-α gene is disclosed comprising, inserting the cDNA into an expression vector with a promoter, a transcription/translation terminator, and a ribosome binding site in a medium; replicating the cDNA of PFDN5-α in the medium, and purifying the PFDN5-α-enriched medium. The expression vector may comprise *E. coli* or other organism for harboring the recombinant plasmid, with genes to allow the insertion of eukaryotic sequences.

A kit for enzyme-linked immunosorbent assay (ELISA) detecting the presence of central nervous system leukemia in a patient with B-cell acute lymphoblastic leukemia (B-ALL) is disclosed comprising, a first container for receiving a cell proteome including PFDN5-α from a patient, a second container for receiving a sample of cerebrospinal fluid (CSF) from the patient, a reaction tube configured to mix the cell proteome and the CSF, an optical reading means for observing the reactivity within the reaction tube, and instructions for performing the assay.

BRIEF DESCRIPTION OF THE DRAWINGS

The invention has other advantages and features that will be more readily apparent from the following detailed description of the invention and the appended claims, when taken in conjunction with the accompanying drawings, in which:

DETAILED DESCRIPTION

Figure 1:
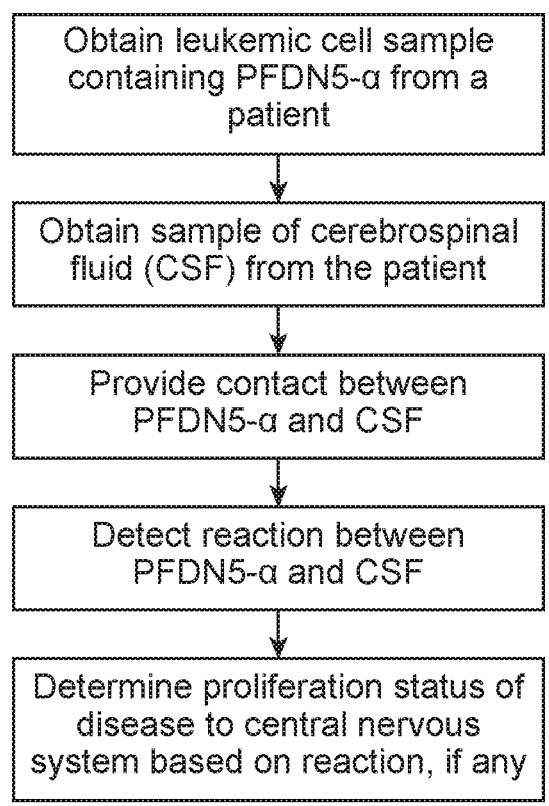
FIG. 1 is a schematic of the general method of identifying CNS proliferation of disease in a patient with B-cell acute lymphoblastic leukemia (B-ALL).

The present disclosure relates to methods and kits for predicting the likelihood of B-ALL patients to undergo CNS relapse. In some aspects, the method uses the reactivity of CSF drawn from the patient to PFDN5-α gene from the leukemia proteome. The CSF from a patient with proliferative disease shows little or no reactivity to PFDN5-α in comparison with a significantly high reactivity of a remission sample with no nervous system proliferation. In some aspects, the method can be used to track disease progression in B-cell acute lymphoblastic leukemia patients throughout the duration of chosen therapy, specifically aiding in classifying CNS-relapse or high risk groups.

In some aspects, methods and kits utilize CSF reactivity patterns to lymphoblast cell proteome, and its association with disease adversity to track disease progression. More specifically, the disclosure described herein provides methods and kits by which early detection of the possibility of developing CNS leukemia in B-ALL patients.

Definitions

The term "PFDN5-α" refers to the polypeptide (SEQ ID NO: 1) of PFDN5-α subunit family encoded by PFDN5-α gene (SEQ ID NO: 2). The encoded protein is one among the six subunits of molecular chaperone complex, PFDN5-α which is involved in the stabilization and proper folding of cytoskeletal proteins. The protein also has a trans-repressional activity to proto-oncogene, c-myc.

"CNS disease/relapse" designates the condition where B-ALL cells have infiltrated the CNS. CNS relapse occurs in less than 10% of acute leukemia cases and requires additional therapy to treat the condition.

The term "CSF at Presentation" indicates, B-ALL CSF samples collected at the time of diagnosis. During this time the patient is clinically 'positive for malignancy' and is very likely to have high percentage of lymphoblasts in the peripheral blood and bone marrow.

The term "CSF at Relapse" is used to point out samples collected at the time of relapse from the B-ALL patient. This condition is also clinically hallmarked with high level of blasts especially in the CNS.

"CSF at Remission" is used to designate B-ALL CSF samples from patients with no observable disease pathophysiology after treatment. In this condition there are no blasts or atypical cells in the peripheral blood and bone marrow and hence denoted as clinically normal.

"Differential Reactivity" refers to variation in CSF reactivity towards PFDN5-α, at different stages of the disease like Presentation/Relapse and Remission.

Detection of CSF Reactivity to PFDN5-α

In one embodiment of the method, a sample of CSF from a B-ALL patient is collected and tagged with biotin as an unbiased sample. The leukemic cell proteome is then incubated with a second sample of biotinylated CSF overnight and incubated with HRP conjugated Streptavidin for a specified time. The reactivity pattern of the leukemic cells with the CSF is then captured and compared with that of the unbiased sample.

The proteins from the leukemic cell that show a differential reactivity of the CSF contain PFDN5-α corresponding to negative CNS leukemia or remission cases, while those samples with less or no reactivity to PFDN5-α correspond to those positive for CNS leukemia at presentation/relapse.

In some embodiments, the method described above is implemented using any known way of detecting protein-protein interactions such as far-western blot test, pull down assay, ELISA, immunoprecipitation or other method known in the art. In one aspect, to obtain a high level of expression of PFDN5-α, a cDNA is inserted into an expression vector with a strong promoter to direct transcription, a transcription/translation terminator, and a ribosome binding site for translational initiation. Additional elements that are typically included in the expression vectors include the Ori site which functions in E. coli, antibiotic resistance gene that permit the selection of bacteria harboring the recombinant plasmid, and unique restriction sites in non-essential regions of the plasmid to allow the insertion of eukaryotic sequences. Subsequently, the expressed PFDN5-α is purified.

In some embodiments, CSF reactivity to PFDN-α is detected using far-western blot test. CSF samples from B-ALL patients are tagged with biotin as an unbiased approach. The leukemic cell proteome on a 2D blot is then incubated with a second sample of the biotinylated CSF overnight. The blot is washed and incubated with HRP conjugated Streptavidin for specified time and incubated with chemiluminescent reaction mixture. The reactivity pattern is then captured on contact X-ray film and compared with the unbiased sample.

In some embodiments, the identification of PFDN-α interacting partners in leukemic patient CSF samples are accomplished by pull down assay using recombinant PFDN5-α. In a pull down assay, the purified his-tagged PFDN5-α is added to the B-ALL CSF and the PFDN5-α interacting partner complex is further precipitated using nickel affinity beads. The proteins or molecules associated with the protein of interest will also be pulled down. The co-precipitated protein can be further identified by western blotting or mass spectrometry or by sequencing of the purified interacting protein.

In some embodiments, the identification of PFDN5-α interacting partners in B-ALL patient CSF samples is accomplished using ELISA method. In one aspect, PFDN5-α interacting partner in the B-ALL CSF is identified by interacting purified PFDN5-α with CSF from patients and measured using a suitable method. The reactivity of the purified PFDN5-α with B-ALL CSF samples may be facilitated by coating the purified PFDN5-α onto ELISA plates, for example. The protein reactivity is identified by a method such as such as optical density or mass spectrometry.

In some embodiments, the identification of PFDN5-α interacting partners in B-ALL patient CSF samples is carried out using immunoprecipitation method. In one aspect, PFDN5-α interacting partner in the B-ALL CSF is identified by interacting purified PFDN5-α with B-ALL CSF from patients and subsequent immunoprecipitation using anti-PFDN5-α antibodies in conjunction with protein A/G and agarose/sepharose beads. Subsequently, the components of the complex are identified by a suitable technique such as optical density, mass spectrometry or other known way of quantifying the reactivity.

In some embodiments, B-ALL CSF reactivity to PFDN5-α protein is used for prognosis or early prediction of CNS disease and for the assortment of patients into different risk groups. For example, the high reactivity to PFDN5-α prognosticates reduced chance of CNS progression and reduced or no reactivity to the same protein in patients undergoing treatment predicts a high risk or the likelihood for CNS disease. The differential reactivity pattern of B-ALL patients to PFDN5-α under different conditions may facilitate the clinicians to stratify the patients into a range of risk groups and aiding them in tailoring the therapeutic regimen according to the patient's assigned risk-group. This could enable clinicians to choose a correct treatment strategy to specifically target the infiltration and monitor the progression after treatment. The identification of the interacting partners of PFDN5-α in the CSF may also help in understanding the biochemistry behind the CNS disease.

Embodiments of the invention are further illustrated in the foregoing examples. The genetic and protein sequences used in the invention are delineated separately.

Example 1: Far-Western Detection of CSF Reactivity to PFDN5-α: CSF Reactivity Profile to Lymphoblastic Proteins on a 2D Blot CSF samples from B-ALL patients were collected in a sequential manner and tagged with biotin as an unbiased approach. The leukemic cell proteome on a 2D blot was incubated with the biotinylated CSF overnight. The blot was washed three times with Tris Buffered Saline (TBS) containing 0.2% Tween 20 and incubated with HRP conjugated Streptavidin for 30 minutes. Again washed in TBST for three times and incubated with chemiluminescent reaction mixture for 1-2 minutes. The reactivity pattern was captured on an X-ray film and compared. Here the leukemic cell proteins on a 2D blot was probed with biotinylated CSF samples from B-ALL patients and detecting the binding affinity of the partners by means of a chemiluminescent reaction.

The results of the blot testing for three patients corresponding to samples A, B and C at different clinical status are shown in FIG. 2A to 2C. In the three figures, the encircled region towards the lower portion corresponds to PFDN5-α reaction. As shown in FIG. 2A, the first sample corresponding to a leukemic patient without CNS leukemia and the third sample corresponding to a patient free of leukemia after treatment (FIG. 2C) show strong PFDN5-α reaction or binding as evidenced by pronounced darkening of the X-ray film at the circled locations. In contrast, sample B corresponding to a patient with CNS leukemia at relapse (FIG. 2B) shows only trace reaction at the PFDN5-α location.

Figure 3:
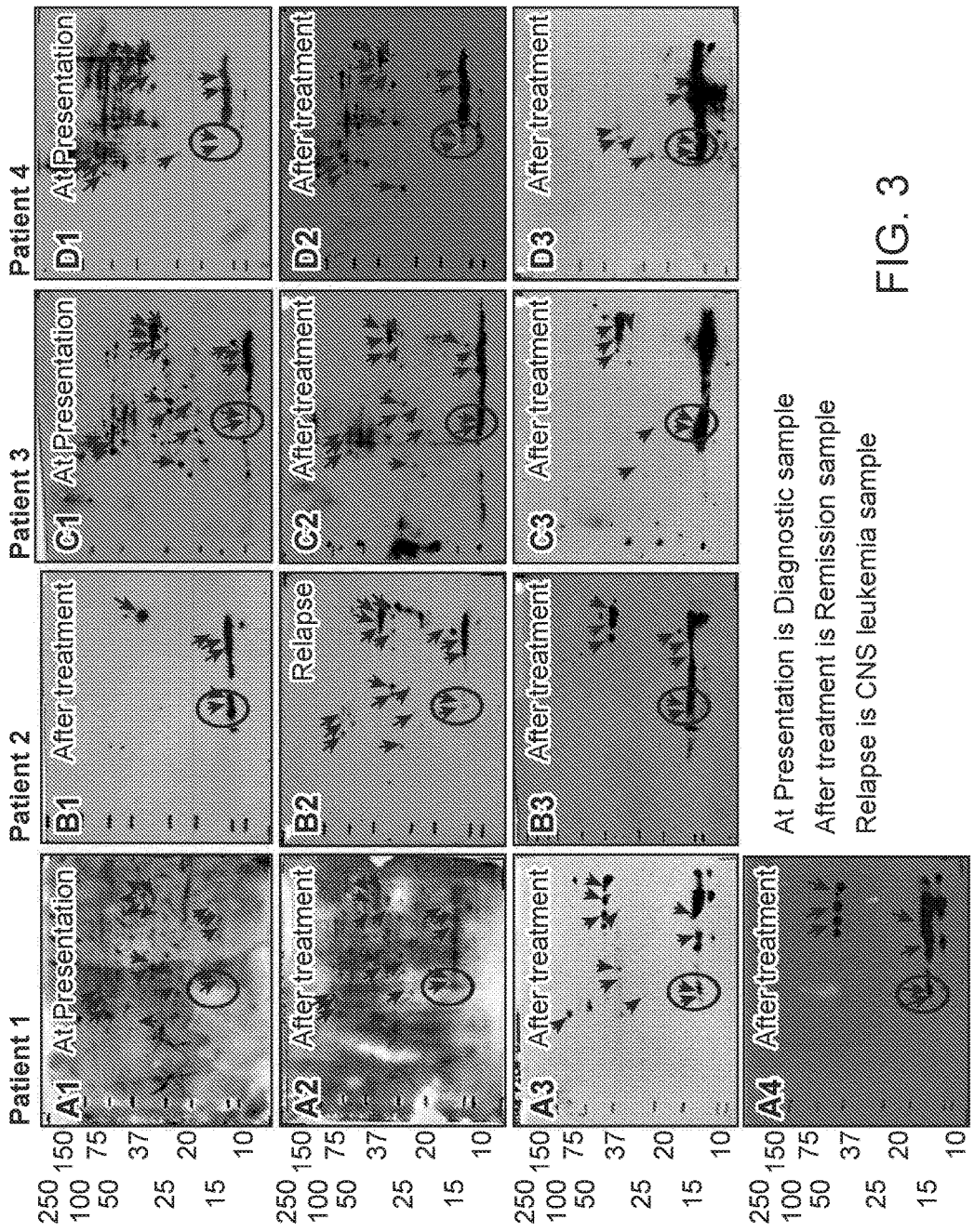
FIG. 3 illustrates consistency in the CSF reactivity profile showing very little or no reactivity in CNS proliferation (A1, B1, D1) and relapse cases (C2) and significantly high reactivity in remission cases after treatment (A4, B3, C3, D3).

The proteins in the encircled regions that showed a differential reactivity on the blot were further analyzed by mass spectrometry and found to contain PFDN5-α. The montage shown in FIG. 3 presents further results from four different patients illustrating application of embodiments of diagnostic methods. Patients 1 to Patient 4 were tested using the embodiments of the invention using the far-western blot test at various stages of treatment, in which absence of reaction showed positive for CNS leukemia and strong reaction showed its absence. The initial stage "At Presentation" tested positive in three cases (A1, B1, and D1), while C1 tested slightly positive and C2 positive because of relapse. The "After Treatment" results were rendered negative (A4, B3, C3, and D3) in all cases because of remission. The experimental results demonstrate that the differential reactivity test results are consistent across patients and different samples and in line with the clinical observations.

Example 2: Image J Quantification of CSF Reactivity to Lymphoblastic Proteins on the 2D Blot In some embodiments, in order to quantify the extent of CSF reactivity shown in FIG. 2, NIH ImageJ software was used. The optical density at the reactive spot corresponding to PFDN5-α was measured using the ImageJ software by making a selection on the spot. Then the background darkening of the same blot was subtracted from the PFDN5-α value and the resulting value considered as PFDN5-α value. Along with this, another spot corresponding to GAPDH which showed reactivity in almost all conditions irrespective of presentation/relapse and remission was also measured in the same way as mentioned above. The value corresponding to GAPDH was used for normalizing the value of PFDN5-α of each sample.

The calculation was done as follows:

$$N_{PFDN5\alpha} = \frac{V_{PFDN5\alpha}}{V_{GAPDH}} \times M_{GAPDH},$$

where
$N_{PFDN5\alpha}$ is normalized value of PFDN5-α
$V_{PFDN5\alpha}$ is value of PFDN5α
$V_{GAPDH}$ is value of GAPDH
$M_{GAPDH}$ is mean value of GAPDH for that particular patient

TABLE 1

Image J Quantification Values and Normalization with GAPDH

|  | CSF | Background | PFDN5α | PFDN5α after background subtraction | GAPDH | GAPDH after background subtraction | normalized value |
|---|---|---|---|---|---|---|---|
| Patient 1 | A1 (CNS involvement) | 83.1 | 85.348 | 2.248 | 181.628 | 98.528 | 2.515 |
|  | A2 | 92.047 | 173.168 | 81.121 | 175.991 | 83.944 | 106.55 |
|  | A3 | 42.086 | 155.668 | 113.582 | 200.776 | 158.69 | 78.92 |
|  | A4 | 83.079 | 113.471 | 30.392 | 182.959 | 99.88 | 33.55 |
|  |  |  |  |  |  | Avg - 110.26 |  |
| Patient 2 | B1 | 65.284 | 234.555 | 169.271 | 223.555 | 158.271 | 153.56 |
|  | B2 (CNS involvement) | 83.094 | 111.218 | 28.124 | 232.218 | 149.124 | 27.08 |
|  | B3 | 116.842 | 246.677 | 129.835 | 240.19 | 123.348 | 151.13 |
|  |  |  |  |  |  | Avg - 143.58 |  |

TABLE 1-continued

Image J Quantification Values and Normalization with GAPDH

|  | CSF | Background | PFDN5α | PFDN5α after background subtraction | GAPDH | GAPDH after background subtraction | normalized value |
|---|---|---|---|---|---|---|---|
| Patient 3 | C1 | 103.593 | 142.333 | 38.74 | 245.926 | 142.333 | 46.23 |
|  | C2 | 60.764 | 249.797 | 189.033 | 248.815 | 188.051 | 170.73 |
|  | C3 | 62.906 | 252.155 | 189.249 | 242.048 | 179.142 | 179.42 |
|  |  |  |  |  |  | Avg - 169.84 |  |
| Patient 4 | D1 | 81.797 | 84.682 | 2.885 | 220.335 | 138.538 | 1.958 |
|  | D2 | 103.134 | 211.377 | 108.243 | 245.452 | 142.318 | 71.53 |
|  | D3 | 51.106 | 249.793 | 198.687 | 52.407 | 1.301 | 14363.548 (not taken due to low GAPDH values) |
|  |  |  |  |  |  | Avg - 94.05 |  |

For calculating the values corresponding to presentation/relapse, the values in Table 1 corresponding to A1, B2, C1 and D1 were averaged and the corresponding values are given in Table 2. Likewise the average of A2, A3, A4, B1, B3, C2, C3 and D2 were also calculated as representative of remission cases in Table 2. The value of D3 was excluded for calculating the average of remission value because it was numerically much higher after normalization with GAPDH because of low GAPDH reactivity.

TABLE 2

Average Values of CSF Reactivity at Presentation/Relapse and Remission

|  | Presentation/Relapse | Remission |
|---|---|---|
| Avg | 19.44506785 | 118.1750816 |
| SD | 21.35370972 | 53.27088725 |
| SE | 5.338427431 | 6.658860906 |

Figure 2:
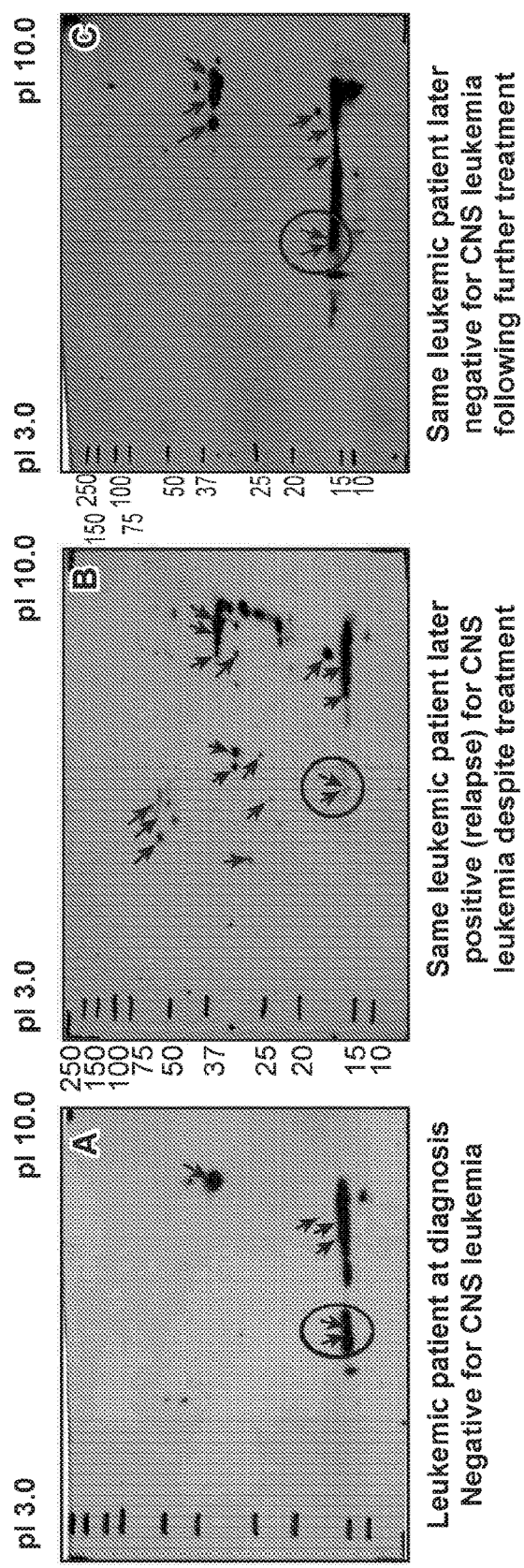
FIG. 2 illustrates far Western blot test results of A) B-ALL patient at presentation, B) B-ALL patient with CNS relapse and C) relapsed patient after treatment.
Figure 4:
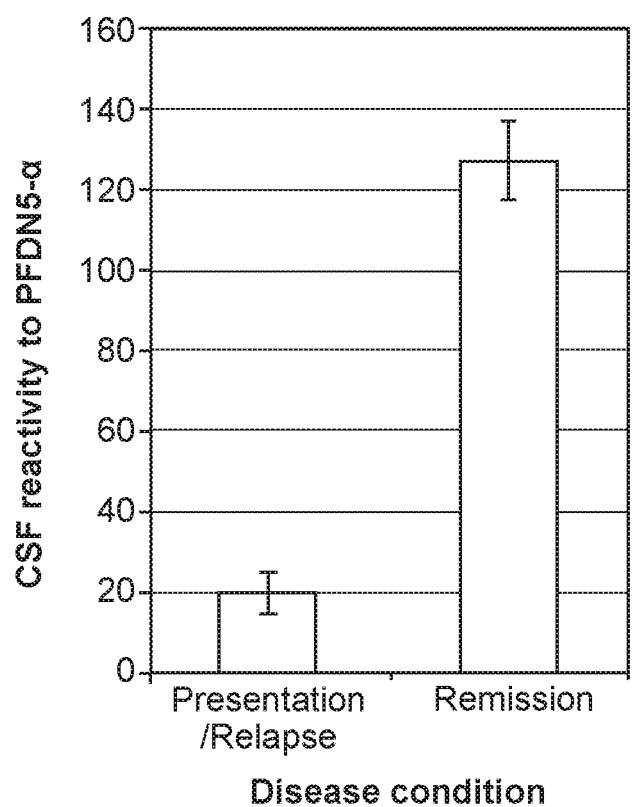
FIG. 4 shows quantitative data (arbitrary units) on difference in the levels of CSF reactivity to PFDN5-α under presentation/relapse and remission conditions.

A quantitative measure of the reactivity tested as illustrated in FIGS. 2 and 3 is shown in FIG. 4, where the difference in the levels of CSF reactivity to PFDN5-α under presentation/relapse and remission conditions is observed. The results of the respective cases are also summarized in Table 3. In the table, the reactivity test results with comments are shown against the sample condition for the four different patients corresponding to the data shown in Table 1 and 2. The average values of these two conditions were plotted on a graph as shown in FIG. 4.

TABLE 3

Summary of CSF Reactivity Tests for PFDN5-α in Four Patients at Various Stages of Treatment

| Condition | PATIENT-1 | PATIENT-2 | PATIENT-3 | PATIENT-4 |
|---|---|---|---|---|
| At Presentation | A1 - positive | B1 - positive | C1 - negative | D1 - positive |

TABLE 3-continued

Summary of CSF Reactivity Tests for PFDN5-α in Four Patients at Various Stages of Treatment

| Condition | PATIENT-1 | PATIENT-2 | PATIENT-3 | PATIENT-4 |
|---|---|---|---|---|
| After Treatment | A2 - positive | B2 - negative | C2 - positive relapsed | D2 - negative |
| After Treatment | A3 - positive | B3 - negative remission | C3 - negative remission | D3 - negative remission |
| After Treatment | A4 - negative remission |  |  |  |

Example 3: Far-Western Analysis Using Bacterially Expressed Pure PFDN5-α Protein: Results of ELISA Quantification In some embodiments, in order to validate and confirm the results of differential reactivity to PFDN5-α observed with and without CNS involvement on the 2D-blot tests, an alternative ELISA analysis was carried out. 5 patients with CNS involvement and 13 patients without CNS involvement and their corresponding sequential treated samples were used for ELISA quantification.

Quantifications of CSF reactivity to PFDN5-α using samples from patients with CNS involvements are now described. Patients 1, 2, 5, 6, and 7 had CNS involvement either at presentation or as relapse. The reactivity to PFDN5-α at the time of CNS involvement and following treatment were used for ELISA quantification.

Patient 1

In Patient 1, CNS involvement was at diagnosis/presentation. Then sequential samples from the same patient following treatment were also collected and analyzed by ELISA along with the sample at presentation and the optical density values (OD) are shown in Table 4.

TABLE 4

OD values of samples at diagnosis with CNS involvement and samples following treatment of Patient 1

| Patient 1 | CNS involvement at diagnosis | Treatment 1 after relapse | Treatment 2 after relapse | Treatment 3 after relapse | Treatment 4 after relapse |
|---|---|---|---|---|---|
| OD1 | 0.072093939 | 0.189274621 | 0.069362667 | 0.190000606 | 0.054497522 |
| OD2 | 0.078765899 | 0.224524095 | 0.090356024 | 0.17599947 | 0.052742044 |

TABLE 4-continued

OD values of samples at diagnosis with CNS involvement
and samples following treatment of Patient 1

| Patient 1 | CNS involvement at diagnosis | Treatment 1 after relapse | Treatment 2 after relapse | Treatment 3 after relapse | Treatment 4 after relapse |
|---|---|---|---|---|---|
| OD3 | 0.061397576 | 0.196764941 | 0.086614361 | 0.159111464 | 0.053930303 |
| Avg | 0.070752471 | 0.203521219 | 0.082111017 | 0.17503718 | 0.05372329 |
| SD | 0.008761525 | 0.01857059 | 0.011197783 | 0.015467038 | 0.000895861 |
| SE | 0.002920508 | 0.006190197 | 0.003732594 | 0.005155679 | 0.00029862 |

Patient 2

In Patient 2, the CNS disease occurred as relapse. Samples were analyzed a) before CNS relapse, b) at CNS relapse, c) after treatment (stage 1) and d) after treatment (stage 2) and used for the quantification according to results in Table 5.

TABLE 5

OD Values of CSF Samples at Different
Stages of the Disease of Patient 2

| Patient 2 | Treatment before relapse | CNS relapse | Treatment 1 after relapse | Treatment 2 after relapse |
|---|---|---|---|---|
| OD1 | 0.19781939 | 0.045271708 | 0.061117306 | 0.11933318 |
| OD2 | 0.255567835 | 0.043498783 | 0.087574684 | 0.108585782 |
| OD3 | 0.259014613 | 0.045989491 | 0.076267717 | 0.102199397 |
| Avg | 0.23746728 | 0.044919994 | 0.074986569 | 0.110039453 |
| SD | 0.034379303 | 0.001282062 | 0.013275135 | 0.008658897 |
| SE | 0.011459768 | 0.000427354 | 0.004425045 | 0.002886299 |

Patient 5

For Patient 5, apart from the initial relapse stage, five stages of treatment were sampled as listed in Table 6.

TABLE 6

OD values of CSF samples at relapse and following treatment of Patient 5

| Patient 5 | CNS relapse | Treatment 1 after relapse | Treatment 2 after relapse | Treatment 3 after relapse | Treatment 4 after relapse | Treatment 5 after relapse |
|---|---|---|---|---|---|---|
| OD1 | 0.056269744 | 0.054726638 | 0.066538392 | 0.082752726 | 0.282847311 | 0.157355464 |
| OD2 | 0.063634721 | 0.048985299 | 0.062744181 | 0.078142328 | 0.319791375 | 0.126426612 |
| OD3 | 0.058610146 | 0.045518392 | 0.061913352 | 0.075633443 | 0.324437649 | 0.132196569 |
| Avg | 0.05950487 | 0.049743443 | 0.063731975 | 0.078842833 | 0.309025445 | 0.138659548 |
| SD | 0.003763127 | 0.004650702 | 0.002465675 | 0.003610966 | 0.022789646 | 0.016446156 |
| SE | 0.001254376 | 0.001550234 | 0.000821892 | 0.001203655 | 0.007596549 | 0.005482052 |

Patient 6

For Patient 6, the relapse sample and three treatment stages were tested.

TABLE 7

OD values of CSF samples at relapse
and following treatment of Patient 6

| Patient 6 | CNS relapse | Treatment 1 after relapse | Treatment 2 after relapse | Treatment 3 after relapse |
|---|---|---|---|---|
| OD1 | 0.044652771 | 0.144647171 | 0.082254556 | 0.101113189 |
| OD2 | 0.046736527 | 0.118269878 | 0.070373963 | 0.088399207 |
| OD3 | 0.040467808 | 0.109497423 | 0.079897614 | 0.10901588 |
| Avg | 0.043952369 | 0.124138157 | 0.077508711 | 0.099509425 |
| SD | 0.003192512 | 0.018294909 | 0.006290251 | 0.010401483 |
| SE | 0.001064171 | 0.006098303 | 0.00209675 | 0.003467161 |

Patient 7

In Patient 7, CNS leukemia occurred as relapse. Before relapse, samples were received from the same patient following treatment after the diagnosis of the disease. Thereafter, the patient had CNS relapse and underwent further treatment. The test results in Table 8 therefore include those from samples before CNS relapse, diagnosed with CNS disease and samples following treatment after relapse.

TABLE 8

OD values of CSF samples at different stages of the disease of Patient 7

| P-7 | T-1 before relapse | T-2 before relapse | CNS relapse | T-1 after relapse | T-2 after relapse | T-3 after relapse | T-4 after relapse | T-5 after relapse |
|---|---|---|---|---|---|---|---|---|
| OD1 | 0.072261 | 0.057669 | 0.109126 | 0.076589 | 0.155417 | 0.324050 | 0.279809 | 0.390513 |
| OD2 | 0.068079 | 0.052786 | 0.106092 | 0.073678 | 0.141397 | 0.302006 | 0.310618 | 0.324993 |
| OD3 | 0.061354 | 0.051895 | 0.075878 | 0.066616 | 0.1474547 | 0.293597 | 0.278942 | 0.327914 |
| Avg | 0.067231 | 0.054117 | 0.0970328 | 0.072294 | 0.1480897 | 0.306551 | 0.289790 | 0.347807 |
| SD | 0.005503 | 0.003108 | 0.0183838 | 0.005128 | 0.007037 | 0.015727 | 0.018043 | 0.037014 |
| SE | 0.001834 | 0.001036 | 0.006128 | 0.001709 | 0.002344 | 0.005242 | 0.006014 | 0.012338 |

Figure 5:
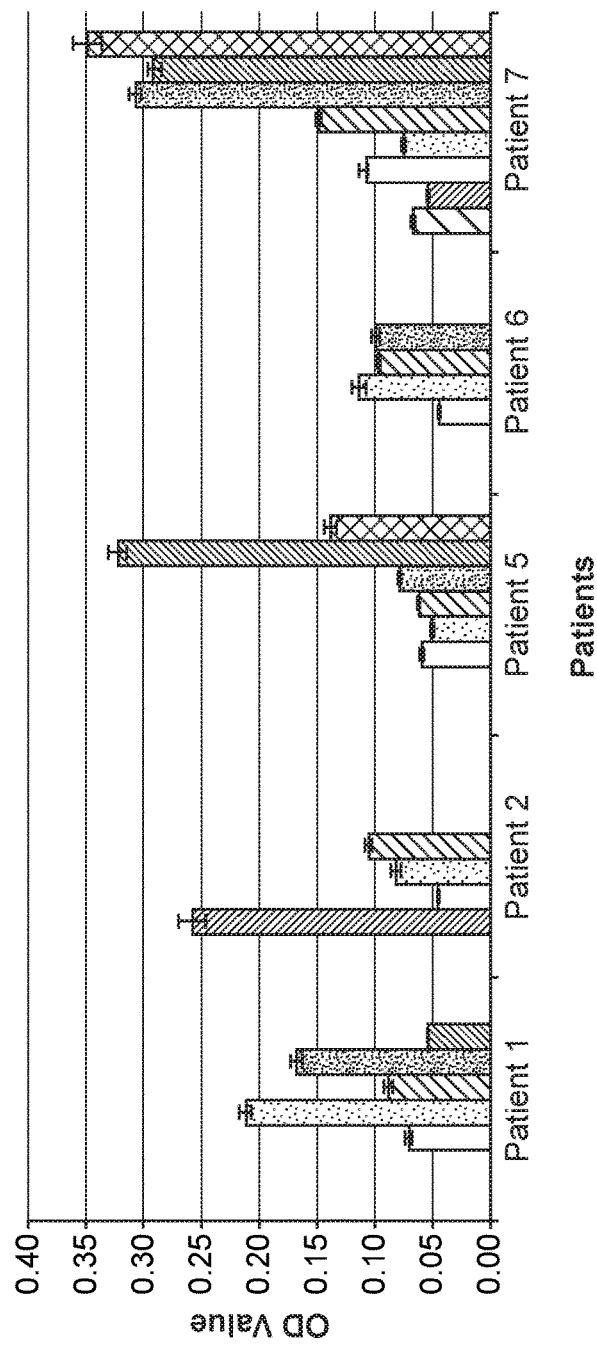
FIG. 5 shows CSF reactivity by ELISA test to PFDN5-α using samples with CNS involvement.

The average of triplicate OD measurement of each condition (relapse, following treatment etc.) of these patients were selected for plotting the graph. The standard error (SE) values were used to plot the error bars. The compiled data for the five patients is given in Table 9 and also shown graphically in FIG. 5. It is observed that there is definite and clear change in reactivity with treatment between the samples at diagnosis and those after treatment, with the latter showing significantly higher reactivity by ~50% higher OD value.

TABLE 9

Average OD values of different clinical conditions of different patients with CNS involvement

| Patient | T-1 before relapse | T-2 before relapse | CNS involvement | T-1 after relapse | T-2 after relapse | T-3 after relapse | T-4 after relapse | T-5 after relapse |
|---|---|---|---|---|---|---|---|---|
| 1 | | | 0.070752 | 0.203521 | 0.082111 | 0.175037 | 0.053723 | |
| 2 | | 0.237467 | 0.044920 | 0.074987 | 0.110039 | | | |
| 5 | | | 0.059505 | 0.049743 | 0.063732 | 0.078843 | 0.309025 | 0.138660 |
| 6 | | | 0.043952 | 0.124138 | 0.077509 | 0.099509 | | |
| 7 | 0.067231 | 0.054117 | 0.097032 | 0.072294 | 0.148089 | 0.306551 | 0.289790 | 0.347807 |

Quantifications of CSF Reactivity to PFDN5α Using Samples from Patients without CNS Involvement are Now Described.

Patients 3, 4, 8, 9, 10, 11, 12, 13, 14, 15, 16, 17 and 18 were cases without CNS involvement. The presentation/diagnostic sample and the sequential samples are collected following treatment. The samples at presentation and sequential samples following treatment of all these patients were used for ELISA quantification and the results are shown in Table 10.

TABLE 10

OD values of patients without CNS involvement

| Patient | Presentation | Treatment 1 | Treatment 2 | Treatment 3 |
|---|---|---|---|---|
| Patient 3 | | | | |
| OD1 | 0.092321655 | 0.149950579 | 0.040747985 | 0.330751099 |
| OD2 | 0.09083777 | 0.147815376 | 0.045167792 | 0.355502843 |
| OD3 | 0.137384524 | 0.115677501 | 0.045220979 | 0.369175754 |
| Avg | 0.106847983 | 0.137814486 | 0.043712252 | 0.351809899 |
| SD | 0.026455826 | 0.019200894 | 0.002567268 | 0.019476702 |
| SE | 0.008818609 | 0.006400298 | 0.000855756 | 0.006492234 |
| Patient 4 | | | | |
| OD1 | 0.142866202 | 0.190066383 | | |
| OD2 | 0.147374053 | 0.181811507 | 0.092723306 | |
| OD3 | 0.12528115 | 0.201217536 | 0.116620457 | |
| Avg | 0.138507135 | 0.191031808 | 0.104671881 | |
| SD | 0.011673696 | 0.009738969 | 0.016897837 | |
| SE | 0.003891232 | 0.003246323 | 0.008448919 | |
| Patient 8 | | | | |
| OD1 | 0.08773261 | 0.107096411 | | 0.138701797 |
| OD2 | 0.096871522 | 0.088413903 | 0.145450545 | 0.10215847 |
| OD3 | 0.080491793 | 0.085136816 | 0.148231233 | 0.090316538 |
| Avg | 0.088365308 | 0.093549043 | 0.146840889 | 0.110392268 |
| SD | 0.008208173 | 0.011846232 | 0.001966244 | 0.025221616 |
| SE | 0.002736058 | 0.003948744 | 0.000983122 | 0.008407205 |
| Patient 9 | | | | |
| OD1 | 0.054485938 | 0.05913601 | | 0.092502085 |
| OD2 | 0.059978521 | 0.054080231 | 0.099385094 | 0.078092436 |
| OD3 | 0.063241159 | 0.057194248 | 0.094714468 | 0.095660838 |
| Avg | 0.059235206 | 0.056803496 | 0.097049781 | 0.088751786 |
| SD | 0.004424688 | 0.002550439 | 0.003302631 | 0.009365402 |
| SE | 0.001474896 | 0.000850146 | 0.001651315 | 0.003121801 |
| Patient 10 | | | | |
| OD1 | 0.156445856 | 0.127807289 | 0.090439599 | 0.207212391 |
| OD2 | 0.135020946 | 0.123085585 | 0.090712936 | 0.149794654 |
| OD3 | 0.11677093 | 0.109851972 | 0.074837263 | 0.176499486 |
| Avg | 0.136079244 | 0.120248282 | 0.085329933 | 0.17783551 |
| SD | 0.019858624 | 0.00930785 | 0.009087946 | 0.028732174 |
| SE | 0.006619541 | 0.003102617 | 0.003029315 | 0.009577391 |
| Patient 11 | | | | |
| OD1 | 0.165878678 | | 0.207892746 | |
| OD2 | 0.166360162 | 0.187634328 | 0.215832332 | |
| OD3 | 0.151577363 | 0.153406808 | 0.205556403 | |
| Avg | 0.161272068 | 0.170520568 | 0.209760494 | |
| SD | 0.008399311 | 0.024202512 | 0.005386561 | |
| SE | 0.00279977 | 0.012101256 | 0.00179552 | |
| Patient 12 | | | | |
| OD1 | 0.068812222 | 0.06197763 | 0.065597521 | 0.066460135 |
| OD2 | 0.0670312 | 0.064832634 | 0.067638868 | 0.069772712 |
| OD3 | 0.104657283 | 0.068492864 | 0.067657527 | 0.083146118 |
| Avg | 0.080166902 | 0.065101043 | 0.066964639 | 0.073126322 |
| SD | 0.021227979 | 0.003265899 | 0.001183996 | 0.008834055 |
| SE | 0.007075993 | 0.001088633 | 0.000394665 | 0.002944685 |
| Patient 13 | | | | |
| OD1 | 0.076821548 | 0.07293506 | 0.063906491 | 0.081057172 |
| OD2 | 0.078493032 | 0.075286723 | 0.065599758 | 0.091074711 |
| OD3 | 0.088018512 | 0.070451936 | 0.072364482 | 0.072620891 |
| Avg | 0.081111031 | 0.07289124 | 0.067290243 | 0.081584258 |
| SD | 0.006040152 | 0.002417691 | 0.004475233 | 0.009238194 |
| SE | 0.002013384 | 0.000805897 | 0.001491744 | 0.003079398 |
| Patient 14 | | | | |
| OD1 | 0.166207923 | 0.099995722 | 0.115596646 | 0.119013801 |
| OD2 | 0.152603483 | 0.097128323 | 0.115593345 | 0.121302527 |
| OD3 | 0.142553509 | 0.080859777 | 0.12716795 | 0.121897037 |
| Avg | 0.153788305 | 0.092661274 | 0.119452647 | 0.120737788 |
| SD | 0.011871633 | 0.010320465 | 0.006681649 | 0.001522321 |
| SE | 0.003957211 | 0.003440155 | 0.002227216 | 0.00050744 |
| Patient 15 | | | | |
| OD1 | 0.152580878 | 0.079342617 | 0.105461965 | 0.096354068 |
| OD2 | 0.143911951 | 0.072425326 | 0.1128678 | 0.112861357 |
| OD3 | 0.157141971 | 0.076660182 | 0.132366132 | 0.115779289 |
| Avg | 0.1512116 | 0.076142708 | 0.116898632 | 0.108331571 |
| SD | 0.009355037 | 0.002994495 | 0.013787403 | 0.00206329 |
| SE | 0.004677518 | 0.001497248 | 0.006893701 | 0.001031645 |

TABLE 10-continued

OD values of patients without CNS involvement

| Patient | Presentation | Treatment 1 | Treatment 2 | Treatment 3 |
|---|---|---|---|---|
| Patient 16 | | | | |
| OD1 | 0.165962278 | 0.11183246 | 0.149262811 | 0.183949453 |
| OD2 | 0.208005927 | 0.110539599 | 0.155995493 | 0.177025366 |
| OD3 | 0.172468685 | 0.154051286 | 0.185351286 | 0.162005294 |
| Avg | 0.18214563 | 0.125474448 | 0.16353653 | 0.174326704 |
| SD | 0.022630721 | 0.024756708 | 0.019189709 | 0.011218227 |
| SE | 0.007543574 | 0.008252236 | 0.00639657 | 0.003739409 |
| Patient 17 | | | | |
| OD1 | 0.180190984 | 0.197047065 | 0.19755663 | 0.173385827 |
| OD2 | 0.186190616 | 0.197226998 | 0.192501111 | 0.159678892 |
| OD3 | 0.161294958 | 0.203063993 | 0.213007072 | 0.221114958 |
| Avg | 0.175892186 | 0.199112685 | 0.201021604 | 0.184726559 |
| SD | 0.012992621 | 0.003423115 | 0.010683077 | 0.03224991 |
| SE | 0.004330874 | 0.001141038 | 0.003561026 | 0.01074997 |
| Patient 18 | | | | |
| OD1 | 0.123727995 | 0.138098623 | 0.096449682 | 0.114650653 |
| OD2 | 0.135726098 | 0.126393661 | 0.103206767 | 0.116988145 |
| OD3 | 0.141913949 | 0.111297168 | 0.092846872 | 0.119172184 |
| Avg | 0.133789347 | 0.125263151 | 0.097501107 | 0.116936994 |
| SD | 0.009246377 | 0.013436444 | 0.005259371 | 0.0022612 |
| SE | 0.003082126 | 0.004478815 | 0.001753124 | 0.000753733 |

Figure 6:
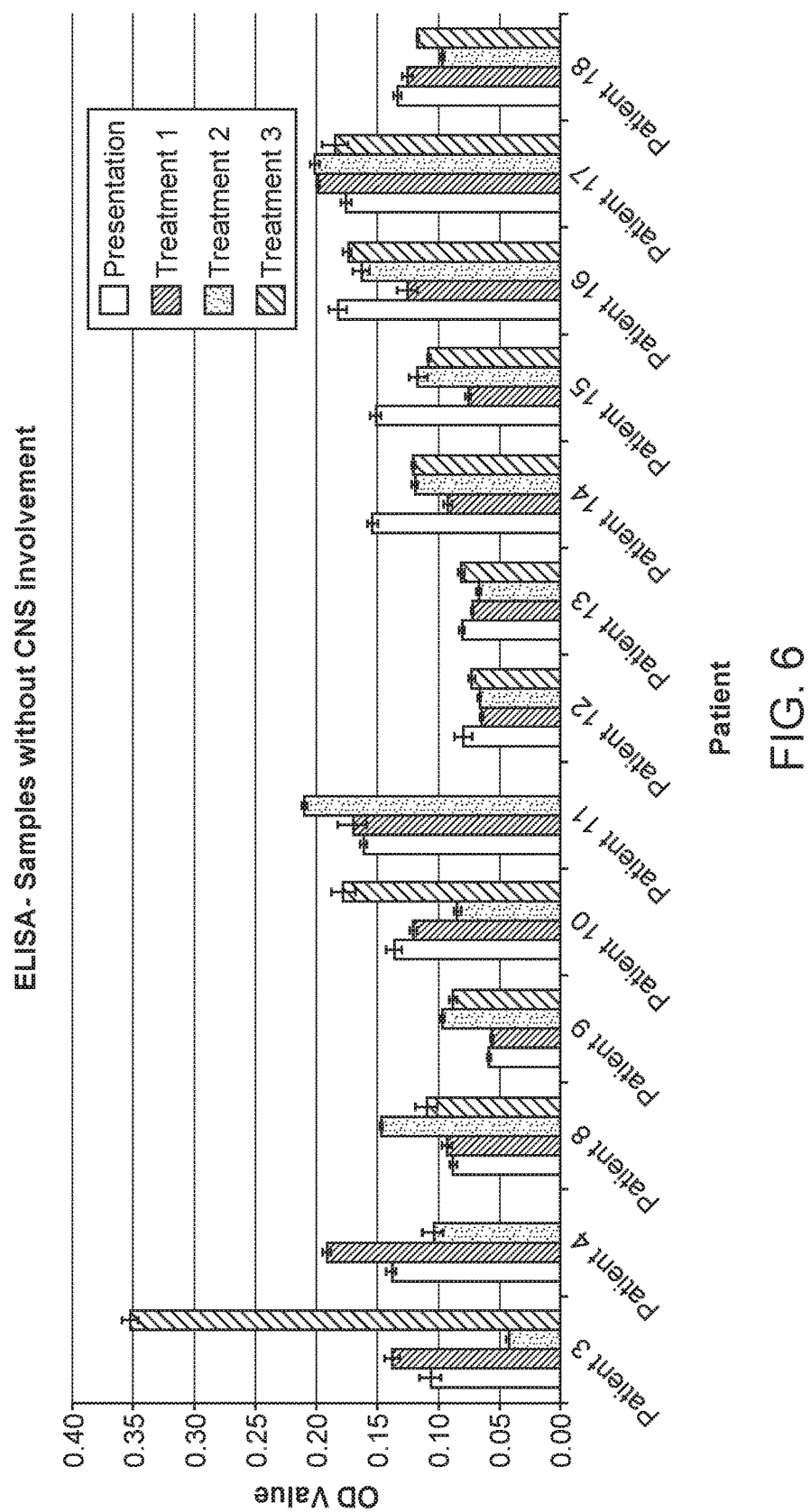
FIG. 6 shows CSF reactivity by ELISA test to PFDN5-α using samples free of CNS involvement.

The average of triplicate OD measurements of each condition for these patients was plotted on a graph as shown in FIG. 6. The standard error (SE) values were used to plot the error bars. The compiled data for the graphical representation is given below in Table 11. The data in FIG. 6 show that in the patients where there was no CNS disease involvement, there was either significant reactivity in all cases or no significant change in reactivity at different treatment stages, unlike in the data for CNS diseased patients shown in FIG. 5.

TABLE 11

Average OD values of patients at different clinical conditions which were used for the graphical representation

| Patient | Presentation | Treatment 1 | Treatment 2 | Treatment 3 |
|---|---|---|---|---|
| Patient 3 | 0.106847983 | 0.137814486 | 0.043712252 | 0.351809899 |
| Patient 4 | 0.138507135 | 0.191031808 | 0.104671881 | |
| Patient 8 | 0.088365308 | 0.093549043 | 0.146840889 | 0.110392268 |
| Patient 9 | 0.059235206 | 0.056803496 | 0.097049781 | 0.088751786 |
| Patient 10 | 0.136079244 | 0.120248282 | 0.085329933 | 0.17783551 |
| Patient 11 | 0.161272068 | 0.170520568 | 0.209760494 | |
| Patient 12 | 0.080166902 | 0.065101043 | 0.066964639 | 0.073126322 |
| Patient 13 | 0.081111031 | 0.07289124 | 0.067290243 | 0.081584258 |
| Patient 14 | 0.153788305 | 0.092661274 | 0.119452647 | 0.120737788 |
| Patient 15 | 0.1512116 | 0.076142708 | 0.116898632 | 0.108331571 |
| Patient 16 | 0.18214563 | 0.125474448 | 0.16353653 | 0.174326704 |
| Patient 17 | 0.175892186 | 0.199112685 | 0.201021604 | 0.184726559 |
| Patient 18 | 0.133789347 | 0.125263151 | 0.097501107 | 0.116936994 |

For comparison of ELISA results with control values, the values samples with CNS involvement (from Table 9) were averaged for the 5 patients as representative of those with CNS involvement. Then, the average of corresponding samples after treatment was also calculated from the same patients as representative value of samples with CNS involvement following treatment. Likewise the samples without CNS involvement and their corresponding samples after treatment were also selected (Table 10 and 11) and averaged. These values are presented in Table 13.

Subsequently, these CSF reactivity values of CNS involvement and without CNS involvement and their corresponding treated sample values were compared with that of control samples without any malignancy and CNS disease. The control samples used were pyrexia, Down's syndrome, Type II diabetics and vascular headache. OD values for control samples for four non-malignant disease states are given in Table 12. The CSF reactivity to PFDN5-α of these different clinical conditions were measured and compared with the leukemia samples.

TABLE 12

OD Values of Control Samples Used for Analysis

| | Pyrexia | Down's Syndrome | Type II Diabetics | Vascular Headache |
|---|---|---|---|---|
| | 0.22755197 | 0.162691052 | 0.192306433 | 0.156793586 |
| | 0.216909719 | 0.16500872 | 0.159758464 | 0.153853423 |
| | 0.207824244 | 0.165400317 | 0.166590604 | 0.152593715 |
| Avg | 0.217428644 | 0.164366697 | 0.172885167 | 0.154413575 |
| SD | 0.009874095 | 0.0014643 | 0.017162713 | 0.00215524 |
| SE | 0.003291365 | 0.0004881 | 0.005720904 | 0.000718413 |

For each experiment the CSF reactivity to bovine serum albumin (BSA) was calculated to get the basal reactivity. The average of all these values was taken for the compiled data presentation as shown in Table 13.

TABLE 13

Basal reactivity of CSF to BSA

| Instance | Basal reactivity (BSA + CSF) |
|---|---|
| 1 | 0.036144444 |
| 2 | 0.03698 |
| 3 | 0.03879 |
| 4 | 0.03643 |
| 5 | 0.0367 |
| 6 | 0.041484848 |
| 7 | 0.036689394 |
| 8 | 0.038095455 |
| 9 | 0.038139394 |
| 10 | 0.044423333 |
| 11 | 0.046634848 |
| 12 | 0.039137429 |
| Avg | 0.039137429 |
| SD | 0.003367512 |
| SE | 0.000280626 |

Figure 7:
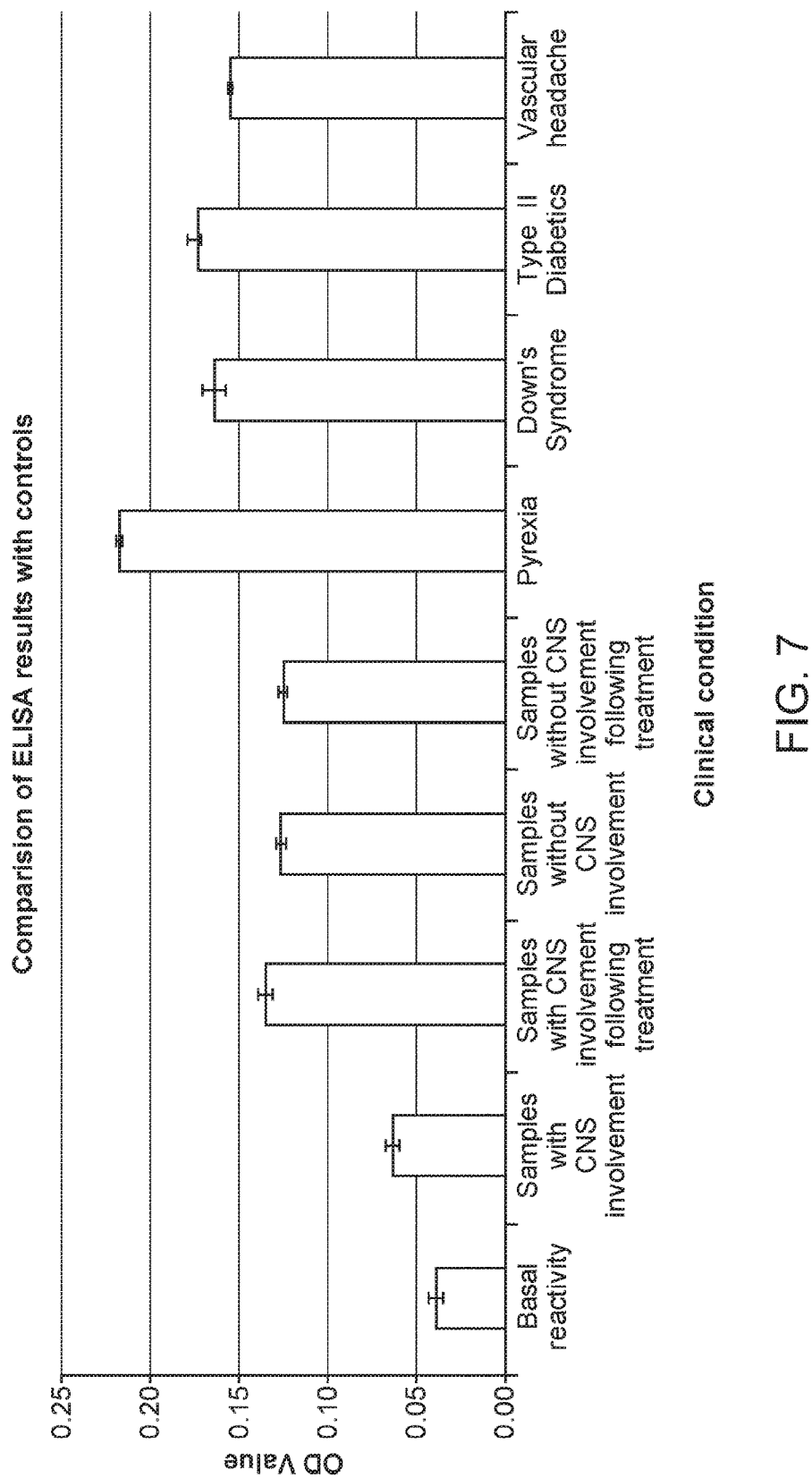
FIG. 7 shows compiled ELISA results showing comparison between CSF reactivity to PFDN5-α of samples with CNS leukemia and without CNS leukemia involvement, samples from treated patients and control samples without any malignancy.

ELISA results of samples with and without CNS involvement and corresponding samples following treatment are shown compared against the reactivity of basal and control samples in Table 14. The data represent averaged data from CNS diseased (Table 9) as well as disease-free patients (Table 11) as well as control samples (Table 12 and 13). The results are also graphically represented in FIG. 7, along with the corresponding statistical variance of data. The results show that the samples with CNS involvement are clearly distinguishable from those free of CNS disease or those taken after remission, and from any of the other control data including basal data. The CNS diseased samples show only 50% or less of reactivity as represented by OD values, compared to the treated and remission samples.

Comparison of the results of the far western 2D blot test and ELISA shows that the disease prevalence of CNS leukemia is clearly and distinguishably identified using both the methods, through measurement of reactivity between cerebrospinal fluid and PFDN5-α derived from leukemia proteome. The methods of the invention therefore provide a means to reliably identify prevalence of CNS leukemia in B-ALL patients.

TABLE 14

Compiled data of CSF reactivity to PFDN5-α in samples with CNS involvement and without CNS involvement and their corresponding samples after treatment, along with control samples

| Sample Description | OD |
|---|---|
| Basal reactivity | 0.0391374 |
| Samples with CNS involvement | 0.0632324 |
| Samples with CNS involvement following treatment | 0.135812 |
| Samples without CNS involvement | 0.1268009 |
| Samples without CNS involvement following treatment | 0.1252758 |
| Pyrexia | 0.2174286 |
| Down's Syndrome | 0.1643667 |
| Type II Diabetics | 0.1728852 |
| Vascular headache | 0.1544136 |

Also disclosed herein are kits for prognosis/detection of CNS disease. In some embodiments, the kit for this application includes the following: assay reagents, buffers, reaction tubes, ELISA model PFDN5-α coated plates etc. The product may include sterile saline or any other pharmaceutically suitable emulsion and suspension base. In addition, the kit may include written or printed instructional materials containing directions i.e. protocols for the practice of the methods of this invention.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

What is claimed is:

1. A method of predicting leukemia of the central nervous system (CNS) in B-cell acute lymphoblastic leukemia (B-ALL) patients, comprising:
   a) obtaining a sample of cerebrospinal fluid (CSF) from a B-ALL patient;
   b) biotinylating the sample;
   c) applying the biotinylated sample to a control sample including a PFDN5-α protein;
   d) detecting a level of binding of the biotinylated sample with the PFDN5-α protein; and
   e) comparing the level of binding of the biotinylated sample against a threshold of significance, wherein the threshold of significance is a predetermined level of binding of the biotinylated sample to a standard protein representing non-specific binding to CSF, wherein the B-ALL patient is detected as negative for CNS leukemia when the level of binding is greater than the threshold of significance by at least 50%.

2. The method of claim 1, wherein detecting the level of binding of the biotinylated sample with the PFDN5-α protein comprises testing using far-western blot test, a pull down assay, an ELISA test or immunoprecipitation.

3. A method of managing treatment in a patient with B-cell acute lymphoblastic leukemia (B-ALL) by predicting central nervous system (CNS) leukemia, comprising:
   a) obtaining a sample of cerebrospinal fluid (CSF) from the patient;
   b) biotinylating the sample;
   c) applying the biotinylated sample to a control sample including PFDN5-α protein;
   d) detecting a level of binding of the biotinylated sample with the PFDN5-α protein;
   e) comparing the level of binding of the sample against a threshold of significance, wherein the threshold of significance is a predetermined level of binding of the biotinylated sample to a standard protein representing non-specific binding to CSF, wherein the B-ALL patient is detected as negative for CNS leukemia when the level of binding is greater than the threshold of significance by at least 50%;
   f) determining the patient is not negative for CNS leukemia; and
   g) treating the patient for CNS leukemia.

4. The method of claim 3, wherein detecting the level of binding of the biotinylated sample with the PFDN-α protein comprises testing using far-western blot test, a pull down assay, an ELISA test or immunoprecipitation.

* * * * *

SEQUENCE LISTING

```
<160> NUMBER OF SEQ ID NOS: 2

<210> SEQ ID NO 1
<211> LENGTH: 154
<212> TYPE: PRT
<213> ORGANISM: Homo sapiens

<400> SEQUENCE: 1

Met Ala Gln Ser Ile Asn Ile Thr Glu Leu Asn Leu Pro Gln Leu Glu
1               5                   10                  15

Met Leu Lys Asn Gln Leu Asp Gln Glu Val Glu Phe Leu Ser Thr Ser
            20                  25                  30

Ile Ala Gln Leu Lys Val Val Gln Thr Lys Tyr Val Glu Ala Lys Asp
        35                  40                  45

Cys Leu Asn Val Leu Asn Lys Ser Asn Glu Gly Lys Glu Leu Leu Val
    50                  55                  60

Pro Leu Thr Ser Ser Met Tyr Val Pro Gly Lys Leu His Asp Val Glu
65                  70                  75                  80

His Val Leu Ile Asp Val Gly Thr Gly Tyr Tyr Val Glu Lys Thr Ala
                85                  90                  95

Glu Asp Ala Lys Asp Phe Phe Lys Arg Lys Ile Asp Phe Leu Thr Lys
            100                 105                 110

Gln Met Glu Lys Ile Gln Pro Ala Leu Gln Glu Lys His Ala Met Lys
        115                 120                 125

Gln Ala Val Met Glu Met Met Ser Gln Lys Ile Gln Gln Leu Thr Ala
    130                 135                 140

Leu Gly Ala Ala Gln Ala Thr Ala Lys Ala
145                 150

<210> SEQ ID NO 2
<211> LENGTH: 743
<212> TYPE: DNA
<213> ORGANISM: Homo sapiens

<400> SEQUENCE: 2
gaggatcata gagctgtctg gcgcagcgag gcctcccggc gccaccgaga cgcgcagagg      60
acggctagag cgttgctcgc cgagagactt cctcttcgtt aagtcggcct tcccaacatg     120
gcgcagtcta ttaacatcac ggagctgaat ctgccgcagc tagaaatgct caagaaccag     180
ctggaccagg aagtggagtt cttgtccacg tccattgctc agctcaaagt ggtacagacc     240
```

-continued

```
aagtatgtgg aagccaagga ctgtctgaac gtgctgaaca agagcaacga ggggaaagaa      300
ttactcgtcc cactgacgag ttctatgtat gtccctggga agctgcatga tgtggaacac      360
gtgctcatcg atgtgggaac tgggtactat gtagagaaga cagctgagga tgccaaggac      420
ttcttcaaga ggaagataga ttttctaacc aagcagatgg agaaaatcca accagctctt      480
caggagaagc acgccatgaa acaggccgtc atggaaatga tgagtcagaa gattcagcag      540
ctcacagccc tgggggcagc tcaggctact gctaaggcct gagagttttt gcagaaatgg      600
ggcagaggga cacctttgg gcgtggcttc ctggtgatgg gaagggtctt gtgttttaat       660
gccaataaat gtgccagctg ggcagaaaaa aaaaaaaaaa aaaaaaaaaa aaaaaaaaaa      720
aaaaaaaaaa aaaaaaaaa aaa                                              743
```